United States Patent
Justis et al.

(10) Patent No.: US 7,655,026 B2
(45) Date of Patent: Feb. 2, 2010

(54) EXPANDABLE SPINAL RODS AND METHODS OF USE

(75) Inventors: Jeff R. Justis, Germantwon, TN (US); Hai H. Trieu, Cordova, TN (US)

(73) Assignee: Warsaw Orthopedic, Inc.

( * ) Notice: Subject to any disclaimer, the term of this patent is extended or adjusted under 35 U.S.C. 154(b) by 355 days.

(21) Appl. No.: 11/343,595

(22) Filed: Jan. 31, 2006

(65) Prior Publication Data
US 2007/0191845 A1   Aug. 16, 2007

(51) Int. Cl.
*A61B 17/70* (2006.01)
(52) U.S. Cl. .................. 606/259; 606/246; 606/254; 606/255; 606/257; 606/265
(58) Field of Classification Search .............. 606/61, 606/246, 254, 255, 264, 257, 259, 261, 262, 606/265
See application file for complete search history.

(56) References Cited

U.S. PATENT DOCUMENTS

| | | | | |
|---|---|---|---|---|
| 4,776,337 | A * | 10/1988 | Palmaz | 623/1.11 |
| 5,290,306 | A * | 3/1994 | Trotta et al. | 606/194 |
| 5,972,015 | A * | 10/1999 | Scribner et al. | 606/192 |
| 6,749,614 | B2 | 6/2004 | Teitelbaum et al. | |
| 6,821,277 | B2 | 11/2004 | Teitelbaum | |
| 6,875,212 | B2 * | 4/2005 | Shaolian et al. | 606/61 |
| 6,899,713 | B2 | 5/2005 | Shaolian et al. | |
| 6,964,667 | B2 | 11/2005 | Shaolian et al. | |
| 6,974,460 | B2 * | 12/2005 | Carbone et al. | 606/61 |
| 7,008,424 | B2 * | 3/2006 | Teitelbaum | 606/262 |
| 7,354,419 | B2 * | 4/2008 | Davies et al. | 604/103.06 |
| 7,534,256 | B2 * | 5/2009 | Cragg | 623/1.13 |
| 7,547,324 | B2 * | 6/2009 | Cragg et al. | 623/17.11 |
| 2002/0082598 | A1 | 6/2002 | Teitelbaum | |
| 2003/0004567 | A1 * | 1/2003 | Boyle et al. | 623/1.16 |
| 2003/0091558 | A1 * | 5/2003 | Woolverton | 424/94.64 |
| 2004/0006341 | A1 | 1/2004 | Shaolian et al. | |
| 2004/0133204 | A1 * | 7/2004 | Davies | 606/63 |
| 2005/0015140 | A1 | 1/2005 | deBeer | |
| 2005/0113929 | A1 * | 5/2005 | Cragg et al. | 623/17.16 |
| 2005/0209629 | A1 | 9/2005 | Kerr et al. | |
| 2007/0173939 | A1 * | 7/2007 | Kim et al. | 623/17.11 |

FOREIGN PATENT DOCUMENTS

WO    9934750 A1    7/1999

* cited by examiner

*Primary Examiner*—Eduardo C Robert
*Assistant Examiner*—Ellen Rust

(57) ABSTRACT

A spinal rod includes an elongated tubular member that is inflatable from a first insertion profile to a second enlarged profile. An expandable tubular reinforcement sleeve is concentrically positioned adjacent to the balloon. The balloon may be bonded to the sleeve. The spinal rod may also have longitudinal reinforcement members. A joining member may join two or more of the longitudinal reinforcing members at a discrete point along each. The spinal rod may further include end portions on either side of an inflatable portion.

22 Claims, 10 Drawing Sheets

EXPANDABLE SPINAL RODS AND METHODS OF USE

BACKGROUND

Spinal rods are often used in the surgical treatment of spinal disorders such as degenerative disc disease, disc herniations, scoliosis or other curvature abnormalities, and fractures. Different types of surgical treatments are used. In some cases, spinal fusion is indicated to inhibit relative motion between vertebral bodies. In other cases, dynamic implants are used to preserve motion between attached to the exterior of two or more vertebrae, whether it is at a posterior, anterior, or lateral side of the vertebrae. In other embodiments, spinal rods are attached to the vertebrae without the use of dynamic implants or spinal fusion.

Spinal rods may provide a stable, rigid column that encourages bones to fuse after spinal-fusion surgery. Further, the rods may redirect stresses over a wider area away from a damaged or defective region. Also, a rigid rod may restore the spine to its proper alignment. In some cases, a flexible rod may be appropriate. Flexible rods may provide some advantages over rigid rods, such as increasing loading on interbody constructs, decreasing stress transfer to adjacent vertebral elements while bone-graft healing takes place, and generally balancing strength with flexibility. One disadvantage with conventional rods is that their rigidity and length, which may span several vertebrae, may require large surgical incisions to implant the rod. Therefore, surgical procedures requiring the installation of an elongated rod have often required invasive open procedures that are more costly to perform, and potentially more dangerous and more painful for the patient.

SUMMARY

Illustrative embodiments disclosed herein are directed to a spinal rod having an elongated tubular member that is inflatable with a substance from a first insertion profile to a second enlarged profile. In one embodiment, an expandable tubular reinforcement sleeve may be concentrically positioned relative to a balloon. The reinforcement sleeve may be inside of or outside of the balloon. The reinforcement sleeve may be bonded to the balloon. The substance and an adhesive used to bond the sleeve to the balloon may comprise a preactivated adhesive. The spinal rod may have two or more longitudinal reinforcing members and a joining member joining two or more of the longitudinal reinforcing members at a discrete point along each. The spinal rod may also include end members with the balloon secured at both end members. The balloon may be less wide than the end members when deflated and wider than the end members when inflated.

DETAILED DESCRIPTION

Figure 1:
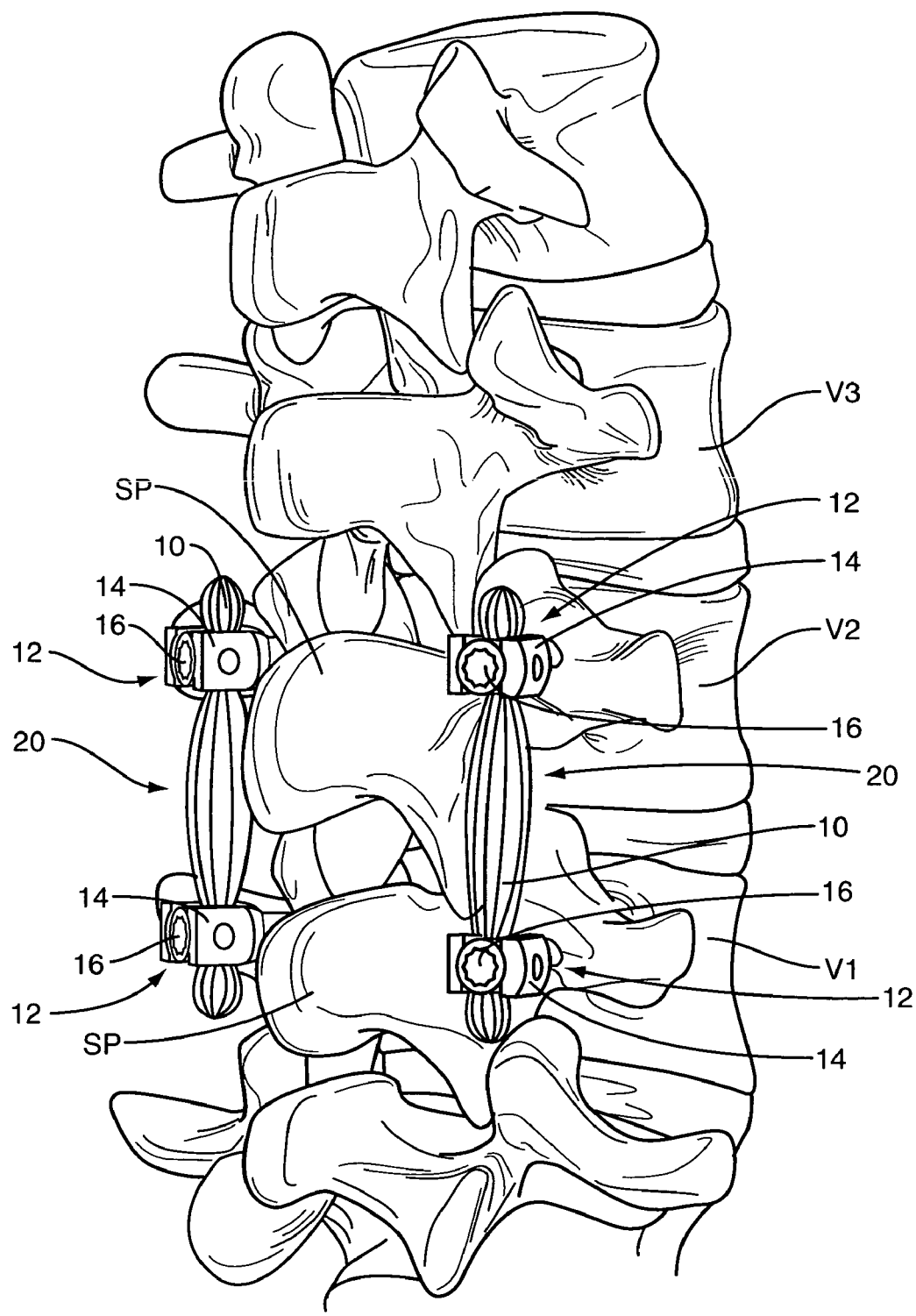
FIG. 1 is a perspective view of first and second assemblies comprising spinal rods attached to vertebral members according to one embodiment.

The various embodiments disclosed herein are directed to spinal rods that are characterized by at least one expandable portion. The expandable portion may be compressed or left unfilled during installation of the rod and may be filled with an injectable substance once the rod is positioned within the body. Similar devices and methods are disclosed in U.S. Pat. No. 6,899,713 to Shaolian et al., the relevant portions of which are incorporated by reference herein. Various embodiments of a spinal rod may be implemented in a spinal rod assembly of the type indicated generally by the numeral 20 in FIG. 1. FIG. 1 shows a perspective view of first and second spinal rod assemblies 20 in which spinal rods 10 are attached to vertebral members V1 and V2. In the example assembly 20 shown, the rods 10 are positioned at a posterior side of the spine, on opposite sides of the spinous processes SP. Spinal rods 10 may be attached to a spine at other locations, including lateral and anterior locations. Spinal rods 10 may also be attached at various sections of the spine, including the base of the skull and to vertebrae in the cervical, thoracic, lumbar, and sacral regions. In one embodiment, a single rod 10 is attached to the spine. Thus, the illustration in FIG. 1 is provided merely as a representative example of one application of a spinal rod 10.

In one embodiment as illustrated in FIG. 1, the spinal rods 10 are secured to vertebral members V1, V2 by pedicle assemblies 12 comprising a pedicle screw 14 and a setscrew 16. In other embodiments, the spinal rod assemblies 20 may be secured to more than two vertebral members, including for example vertebral member V3. The outer surface of spinal rod 10 is grasped, clamped, or otherwise secured between the pedicle screw 14 and setscrew 16. Other mechanisms for securing spinal rods 10 to vertebral members V1, V2 include other types of pedicle screws, hooks, cables, and other such devices. Examples of other types of retaining hardware include threaded caps, screws, and pins. Spinal rods 10 are also attached to plates in other configurations. Thus, the exemplary pedicle assemblies 12 shown in FIG. 1 are merely representative of one type of attachment mechanism.

Figure 2:
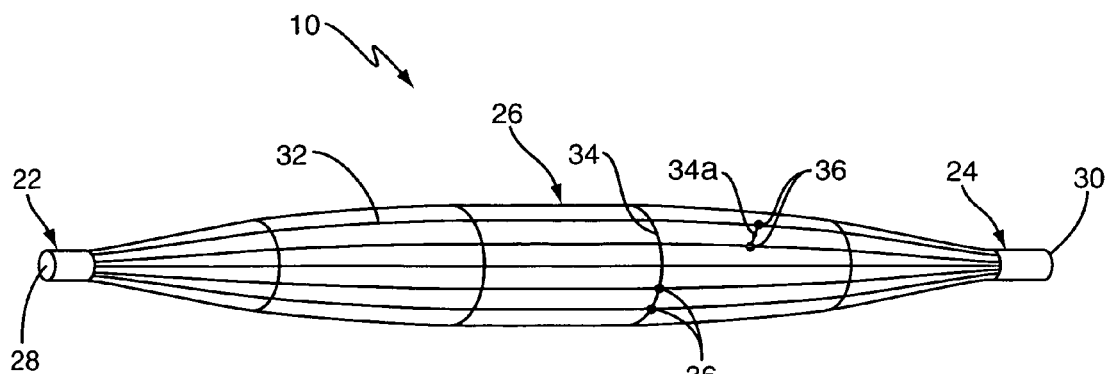
FIG. 2 is perspective view of a spinal rod according to one embodiment.

The spinal rod assemblies 20 comprise an inflatable spinal rod 10 such as the embodiment illustrated in FIG. 2. FIG. 2 shows an elevated perspective view of an inflatable spinal rod 10 in an uninflated state. The spinal rod 10 comprises a first end 22, a second end 24 and a compliant, inflatable balloon 26 between the first end 22 and the second end 24. The balloon 26 may be constructed in a variety of ways, including techniques utilized for balloon angioplasty applications. The first end 22 comprises a self-sealing valve 28, which allows an injectable substance to flow into, but not out of, the balloon 26. The injectable substance that is inserted into the spinal rod 10 may include certain hardenable media, such as epoxy, PMMA, polyurethane, and silicone. Further, the substance may have a lesser or greater viscosity in a cured form as compared to its precured form.

The second end 24 of the spinal rod 10 comprises a tip 30 that is constructed of a biocompatible material. The balloon 26 comprises a suitable complaint biocompatible material, such as a polymer that may include nylon, polyethylene, polyurethane, silicone, polyethylene, polypropylene, polyimide, polyamide, and polyehteretherketone (PEEK). The balloon 26 may be formed from materials that are used in other conventionally known biomedical applications, such as balloon angioplasty. The spinal rod 10 may be reinforced with concentric layers of similar or dissimilar materials and/or fabrics.

Generally, the balloon 26 is an impermeable structure that can be collapsed diametrically for delivery and expanded in situ during implantation. Further, the exemplary balloon 26 comprises thin, reinforcing rails 32 running longitudinally along the balloon 26. Generally, the rails 32 are flexible, but maintain their substantially elongated shape to help the uninflated balloon 26 maintain an elongated shape during insertion (as will be described below). The rails 32 may be constructed of metals such as titanium or nitinol or non-metals such as PEEK, UHMWPE, and carbon-fiber reinforced polymers and resins. The rails 32 may be constructed of other suitable materials as will be understood by those with skill in the art with reference to this disclosure. In one embodiment, the rails 32 extend over substantially the entire proximal to distal length of the balloon 26. In one embodiment, the rails 32 extend over less than the entire proximal length of the balloon 26. The rails 32 may comprise such elements as rods, wires, and cables.

The exemplary spinal rod 10 further comprises a plurality of straps 34 that are secured to the rails 32 at discrete points 36. In one embodiment, the straps 34 are substantially rigid and maintain a substantially circular shape. In one embodiment, the straps 34 maintain a shape of the balloon 26. In one embodiment, the straps 34 are flexible members that allow the rails 32 to expand and contract relative to one another depending on whether the balloon 26 is in a compressed or inflated state. In either case, the straps 34 may maintain a desired spacing between the rails 32. The straps 34 may also prevent the rails 32 from grouping together towards one side of the rod 10 as the injectable substance is inserted into the balloon 26. Also, as shown in FIG. 2, the straps 34 may be disposed at various points along the rails 32, including at or towards the first end 22, at or towards the second end 24, and at intermediate points therebetween. Further, the straps 34 may be used to secure substantially all rails 32 that are disposed in the spinal rod 10. In this case, the straps 34 may be circumferentially disposed within the balloon 26. Alternatively, the straps 34a may be used to secure fewer than all rails 32. In this case, the straps 34 may be radially disposed within the balloon 26. Also, the straps 34, 34a may be oriented normal to, transverse to, or oblique to a longitudinal axis A of the rod 10.

Figure 3:
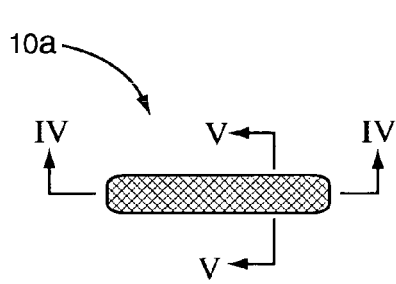
FIG. 3 is a lateral view of a spinal rod according to one embodiment.
Figure 4:
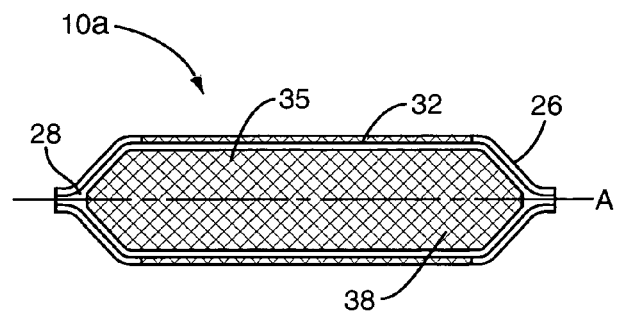
FIG. 4 is a side cross section view of a spinal rod according to one embodiment.

In one embodiment illustrated in FIG. 3, the spinal rod 10a comprises two layers. A detailed cross section of this embodiment of spinal rod 10a is shown in FIG. 4. FIG. 4 also illustrates a self-sealing valve 28 in the form of a duck-bill valve. Other types of one-way valves, including check valves and reed valves, may be used. The self-sealing valve 28 may permit an injectable substance 35 to enter and remain in the balloon 26. The exemplary spinal rod 10a includes a reinforcing structure 38 such as a woven or braided mesh contained within the balloon 26. The reinforcing structure 38 may be constructed of a wide variety of woven or nonwoven fibers, fabrics, metal mesh such as woven or braided wires, polymeric fibers, ceramic fibers, and carbon fibers. Biocompatible fabrics or sheet material such as ePTFE and Dacron®, Spectra®, and Kevlar® may also be used. The use of a braided sleeve may produce higher structural resistance to sheer stress as a result of torsional loads. The braided reinforcing structure 38 may also help distribute the rails 32 in a homogenous manner. The reinforcing structure 38 may have radiographic markers, such as metallic wires, including materials such as gold, platinum or tantalum, disposed therein for visibility of the spinal rod 10 via radiographs or fluoroscopy. Alternatively, a radiopaque material, such as barium sulfate or tantalum powder, may be dispersed among the materials forming the reinforcing structure 38. The expandability and constraining effects provided by the reinforcing structure 38 may also be controlled with the weaving or braiding pattern of the sleeve.

The reinforcing structure 38 may resist kinking of the balloon 26 as the balloon 26 is advanced around corners such as during advancement through an aperture (e.g., portal or eyelet) on a bone anchor 14. As shown, the reinforcing structure 38 may be positioned within the balloon 26. The reinforcing structure 38 may alternatively be embedded within the wall of the balloon 26, or carried on the outside of the balloon 26 much like a conventional stent.

The reinforcing structure 38 may comprise braided fibers that are disposed within the range of from about 15 to about 45 degrees relative to a longitudinal axis A. The braids may be in the form of a plain weave. This braided reinforcing structure 38 may conform dimensionally to the inside diameter of the balloon. In one embodiment, the reinforcing structure 38 has a diameter of about 6 mm.

In the illustrated embodiment, the plurality of longitudinally extending rails 32 is disposed between the balloon 26 and the reinforcing structure 38. In one embodiment, the rails 32 are bonded to the reinforcing structure 38. In one embodiment, the rails 32 are bonded to the balloon 26. In other embodiments, the balloon 26 is disposed interior to the reinforcing structure 38, with the rails 32 disposed therebetween. Some examples of suitable adhesives that may be used to bond the rails 32, balloon 26, straps 34, and reinforcing structure 38 include light curing acrylics and cyanoacrylates, silicones, polyurethanes, and epoxies available from Loctite® of Rocky Hill, Conn., USA. Certain varieties of these materials may also be used as the injectable substance 35. These include light curing adhesives and preactivated epoxies. Preactivated epoxies are one example of an adhesive that will begin to cure once exposed to a certain wavelength of light (e.g., UV, IR), but will not set for some number of minutes thereafter. Thus, in one embodiment, a preactivated epoxy may be used as an injectable substance 35 in the rod 10. The curing process for the preactivated epoxy may be initiated before the rod 10 is inserted into a subject, with a full set occurring after the rod 10 is implanted. That is, the injectable substance may remain fluid or pliable during the installation procedure. For example, the injectable substance (or adhesive) may have a first stiffness at the time when the surgeon begins to insert the rod 10 into the subject. Then, as the substance cures further, the substance may have a second stiffness at the time when the surgeon secures the rod 10 to vertebrae within the subject.

Although a cylindrical configuration for balloon 26 is illustrated herein, any of a variety of alternative cross sectional configurations may be utilized. The overall length, diameter and wall thickness of the spinal rod 10 may be varied, depending on the particular treatment and access site. In one embodiment, the spinal rod 10 has an inflated length between about 20 and 120 mm, and often between about 50 mm and about 80 mm for adjacent vertebrae V1, V2 fixation. Longer lengths may be appropriate where more than two vertebrae V1, V2, V3 are joined to the spinal rod 10. Further, the spinal rod 10 may have an inflated diameter of generally between about 5 mm and 20 mm. The spinal rod 10 may have a deflated diameter of between about 4 mm and 7 mm, which permits installation into conventional rod securing anchors such as pedicle screws 14. Generally, the expandability and constraint of the device may be partially controlled with the balloon 26 diameter and thickness.

Figure 5:
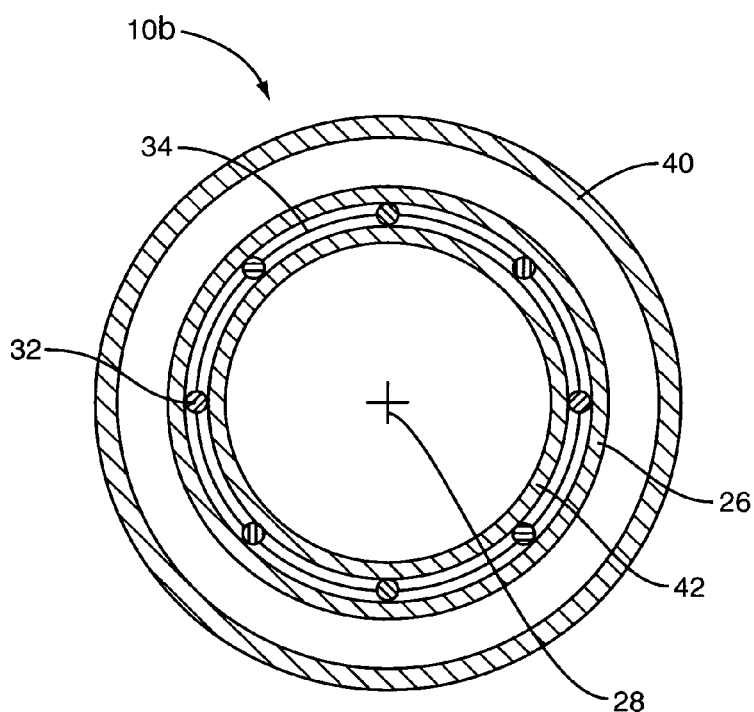
FIG. 5 is an axial cross section view of a spinal rod according to one embodiment.

The construction of an alternative embodiment of a composite spinal rod 10b is illustrated in the cross section view shown in FIG. 5. In this embodiment, an inflatable balloon 26 is provided, as has been discussed. A first reinforcing structure 40 such as a stent, or a braided or woven structure as discussed above is concentrically positioned exterior to the balloon 26. A second reinforcing structure 42 is concentrically disposed within the balloon 26 in the embodiment In one embodiment the first reinforcing structure 42 comprises a diameter of about 5 mm.

The second reinforcing structure 42 is spaced radially inwardly from the first reinforcing structure 40 and the balloon 26. For example, in one embodiment, the second reinforcing structure 42 comprises a diameter of about 4 mm. A plurality of rails 32 is axially oriented within the annular space between the balloon 26 and second reinforcing structure 42. A plurality of rails 32 may also be disposed between the balloon 26 and the first reinforcing structure 40. FIG. 5 also shows a strap 34 joining the rails 32. A variety of alternate constructions can be readily utilized in accordance with the teachings herein. For example, three or more reinforcing structures may be utilized. The layering sequence of the various components may be changed, and other features added or deleted depending upon the desired performance of the finished spinal rod 10. In addition, although the balloon 26 in one embodiment comprises a single layer balloon, other materials may be utilized. In addition, multiple layer balloons may be utilized, with or without reinforcing structures 40, 42 such as stents, wires, or woven tubular support structures disposed therebetween. Further, two or more of the components 26, 32, 40, 42 shown in FIG. 5 may be bonded to one another prior to insertion into a subject patient. The bonds may be formed using biocompatible adhesives, such as those described above.

Figure 6:
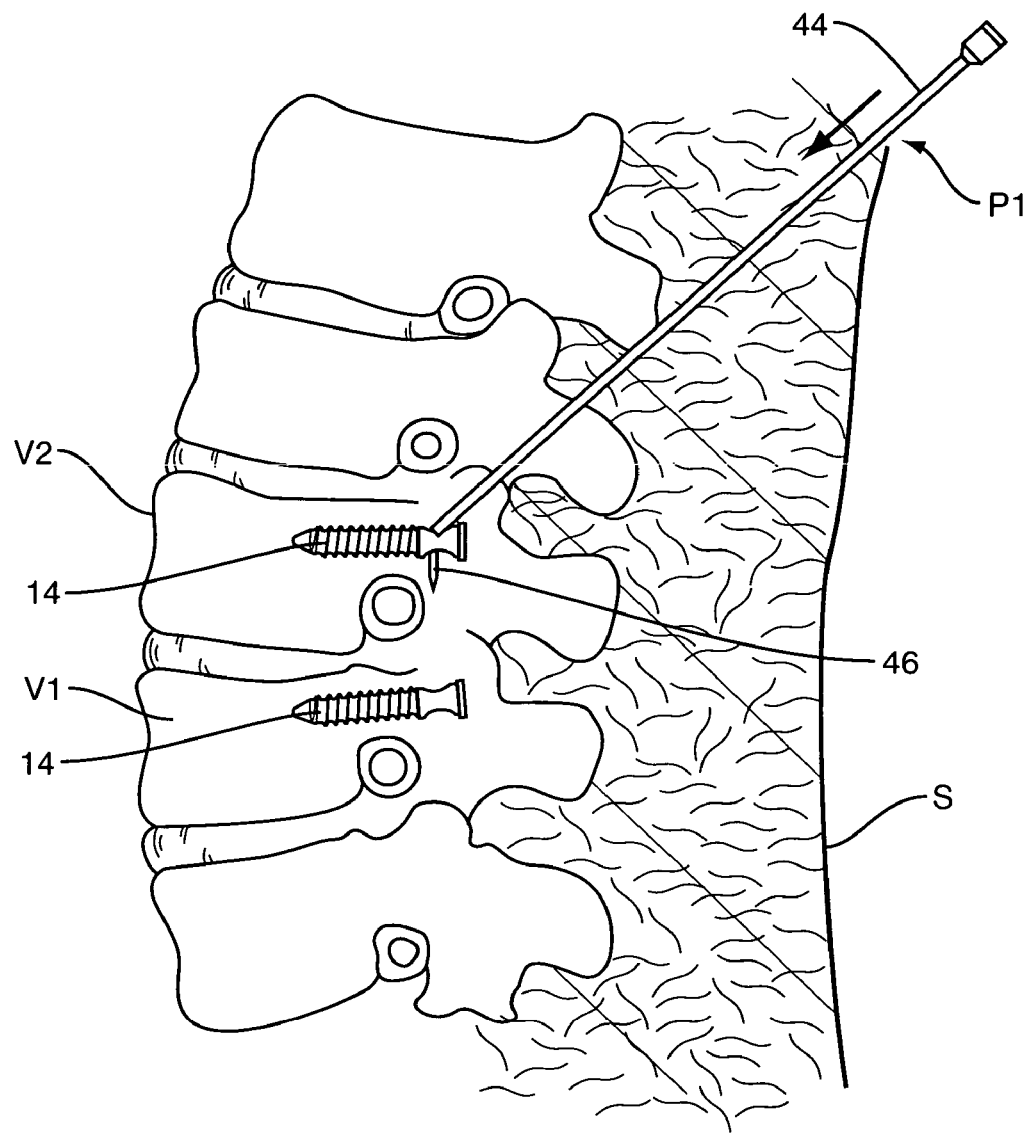
FIGS. 6-10 illustrate one exemplary percutaneous installation technique for installing a spinal rod according to one embodiment.

The embodiments of a spinal rod 10 disclosed herein may be inserted into a patient using a variety of surgical implantation techniques. Certainly, open and mini-open surgical procedures are possible. Percutaneous procedures are also possible. For instance, FIGS. 6-10 illustrate one exemplary percutaneous installation technique. In FIG. 6, a hollow needle 44, such as a 16 gauge or 18 gauge needle, is inserted percutaneously into the subject S at location P1 and advanced to the one of the bone screws 14. While the hollow needle 44 is shown engaging the superior bone screw 14 in vertebrae V2, the hollow needle 44 can initially engage the bone screw 14 in the inferior vertebrae V1.

Figure 7:
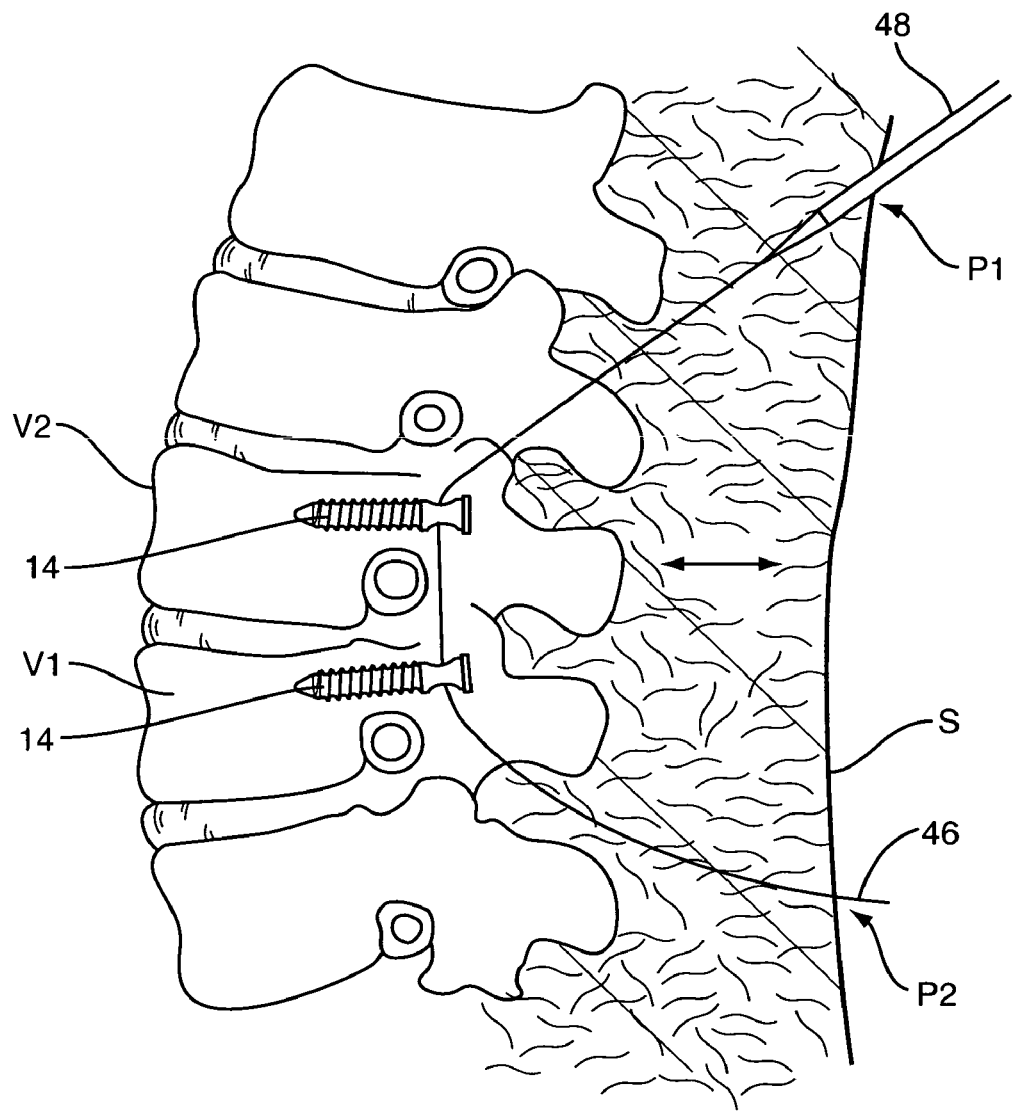

A needle-tipped, semi-rigid guidewire 46 is introduced through the lumen of the hollow needle 44 and through the rod seat in the bone screw 14 in vertebrae V2. The guidewire 46 is directed and advanced towards the second bone screw 14 in vertebrae V1. Certain known techniques for advancing the guidewire 46 may be used. For instance, U.S. Pat. No. 6,899,713 disclosed above presents several techniques. The guidewire 46 is then extracted at a second percutaneous incision P2 as shown in FIG. 7. Then, a flexible introducer sheath 48 is passed over the guidewire 46 along the entire guidewire tract entering incision P1 and exiting incision P2. The guidewire 46 is removed after the introducer sheath 48 is placed.

Figure 8:
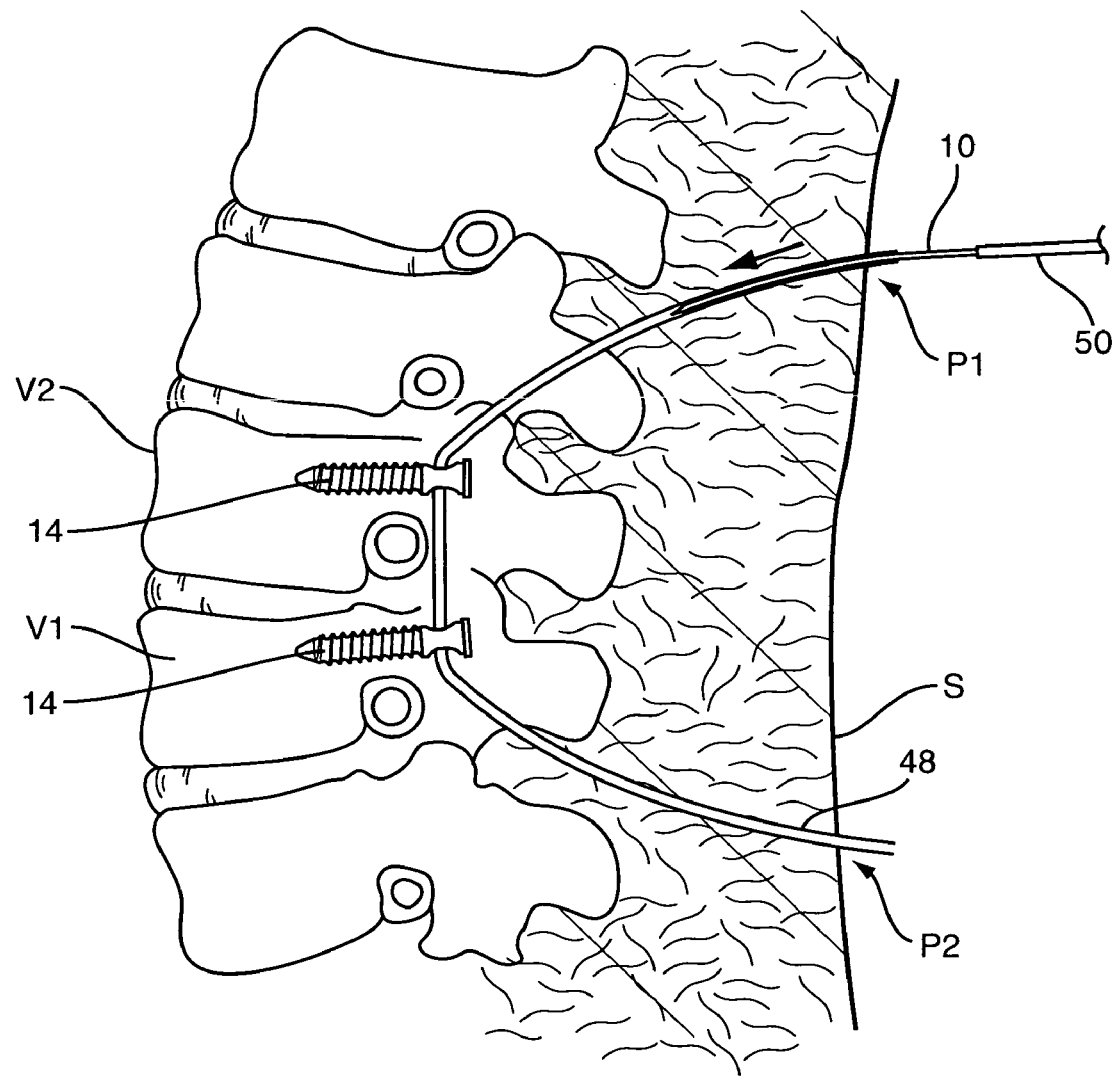

Next, as shown in FIG. 8, an uninflated, inflatable spinal rod 10 is attached to a proximal pushing catheter 50 and advanced through the introducer sheath 48 until the inflatable spinal rod 10 advances between and beyond the two bone screws 14 in vertebrae V1, V2. Once the spinal rod 10 is positioned in or on the bone screws 14, the sheath 48 is removed. At various points in the procedure, the placement of the components, including the spinal rod 10, may be confirmed by fluoroscopy or other radiographic or imaging technique.

Figure 9:
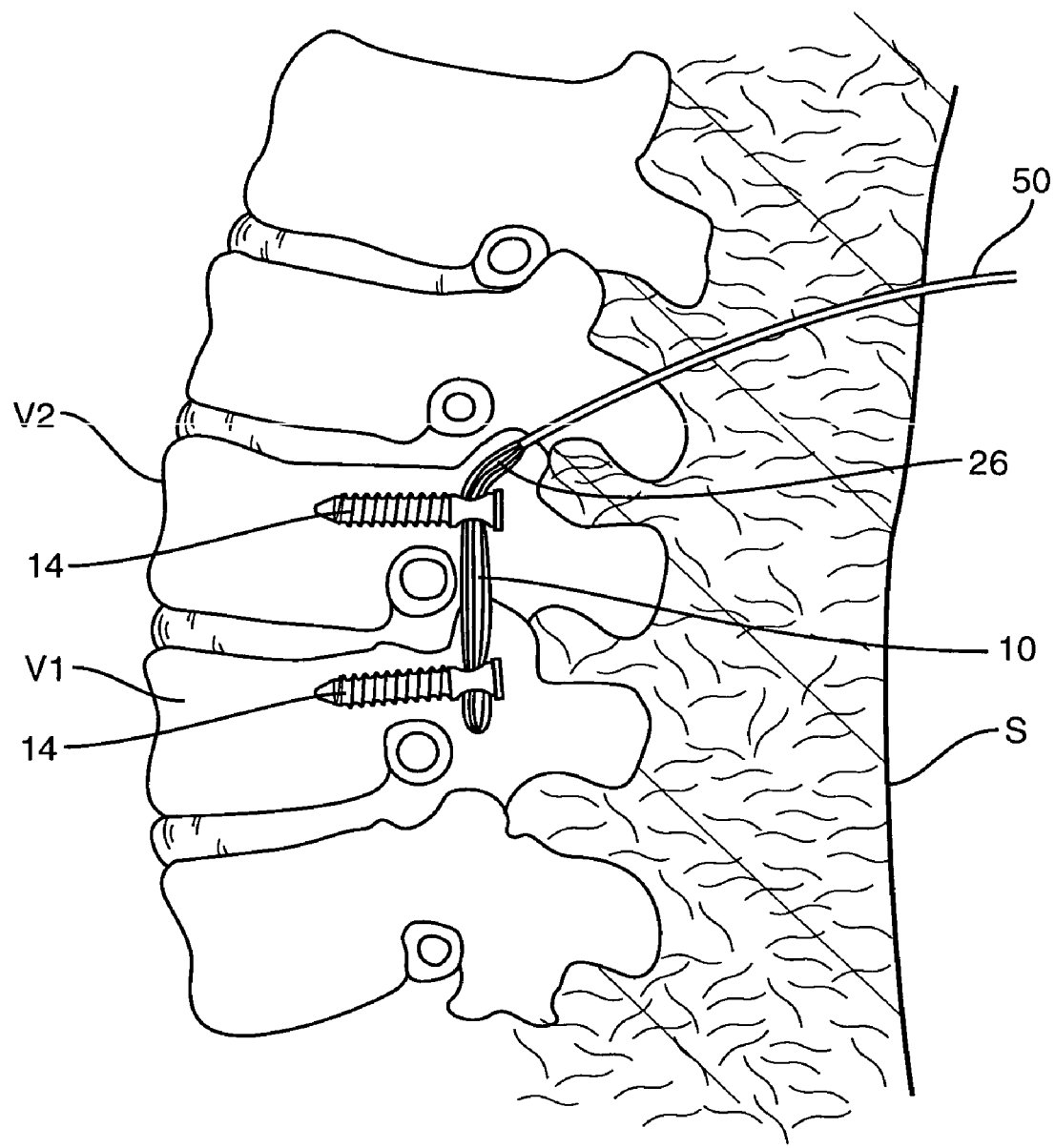

Then, as shown in FIG. 9, the balloon 26 of the inflatable spinal rod 10 is inflated with an injectable substance as disclosed above. The substance may comprise a rapid setting, liquid polymer, or its equivalent, and the polymer is allowed to set. A setscrew 16 (as shown in FIG. 1) or other retaining hardware may be used to secure the spinal rod 10 to each bone screw 14. In one embodiment, the liquid polymer is or includes polymethylmethacrylate or other hardenable media such as those discussed elsewhere herein. In one application, the inflated balloon 26 of the inflatable spinal rod 10 expands longitudinally and radially beyond the head of each bone screw 14, which helps fix the bone screws 14 in relation to each other.

Figure 10:
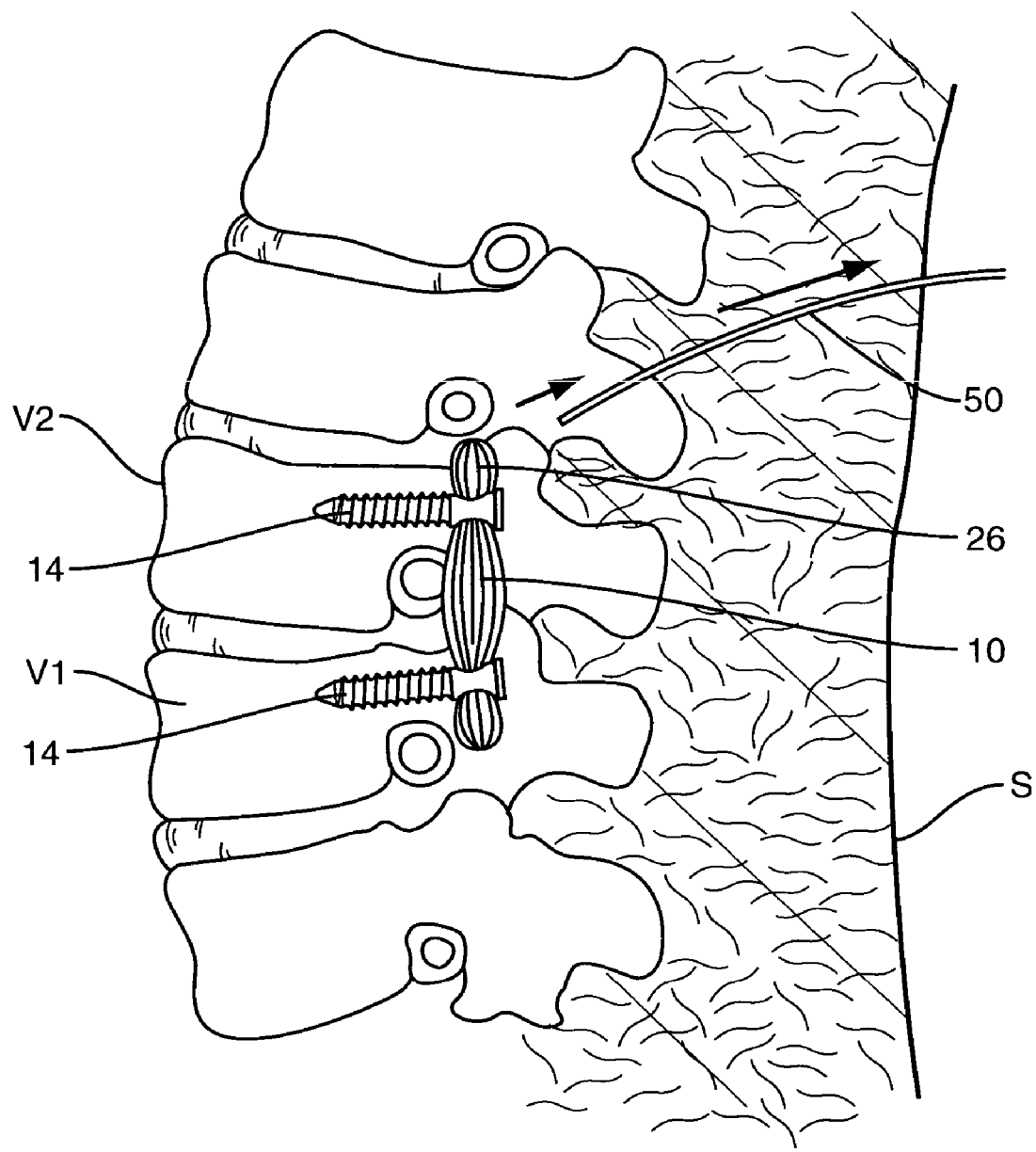

Finally, as shown in FIG. 10, the delivery or pushing catheter 50 is detached from the inflatable spinal rod 10 by pulling on the catheter 50. The method can be repeated on the opposite side of the spinous processes of the subject's S spinal column, thereby repositioning or fixing the one or more unstable, seperated or displaced vertebrae or the one or more portions of one or more vertebrae bilaterally. The percutaneous incisions P1, P2 are closed or sealed as necessary and routine postoperative care administered.

Figure 11:
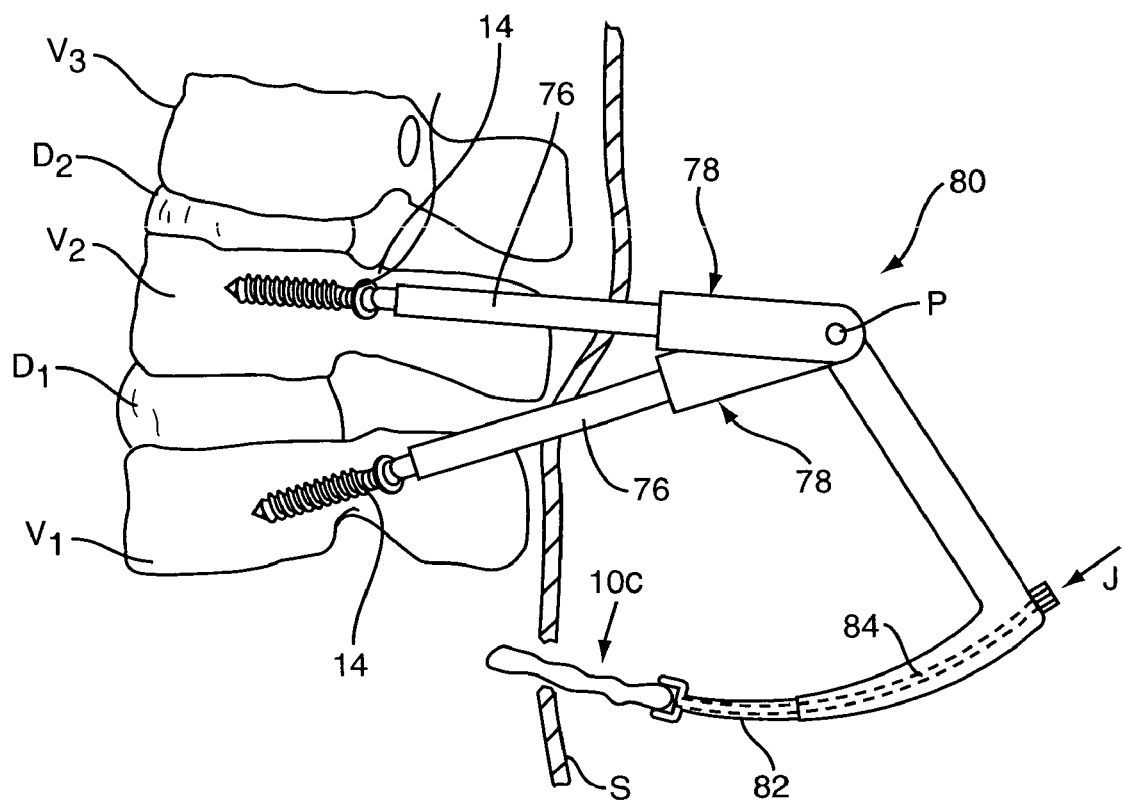
FIG. 11 illustrates one exemplary percutaneous installation technique for installing a spinal rod according to one embodiment.

An alternative installation approach contemplates a minimally invasive percutaneous procedure as shown in FIG. 11. The procedure shown in FIG. 11 incorporates an installation instrument 80. One example of an instrument suitable for this type of installation is the Sextant Rod Insertion System available from Medtronic Sofamor Danek in Memphis, Tenn., USA. The installation instrument includes support arms 78 that are coupled to pedicle screw extensions 76. The support arms 78 are pivotally connected to a rod holder 82 about pivot P. The first and second pedicle screws 14 and pedicle screw extensions 76 are engaged to the first and second vertebrae V1, V2, respectively, through first and second percutaneous punctures in the subject S. If desired, a surgeon can manipulate the pedicle screw extensions 76 to apply a load to compress or distract the vertebrae V1, V2 prior to installing rod 10c. As disclosed above, the uninflated spinal rod 10c may have various structural components, including rails 32 and reinforcing structure 38. In one embodiment, these components 32, 38 may provide sufficient structure for insertion using this illustrated technique. Specifically, the rod 10c is installed through a third percutaneous puncture in the subject S using the installation instrument 20. The rod 10c is brought into engagement with the pedicle screws 14 by rotating the rod holder 82 about pivot P.

Figure 12:
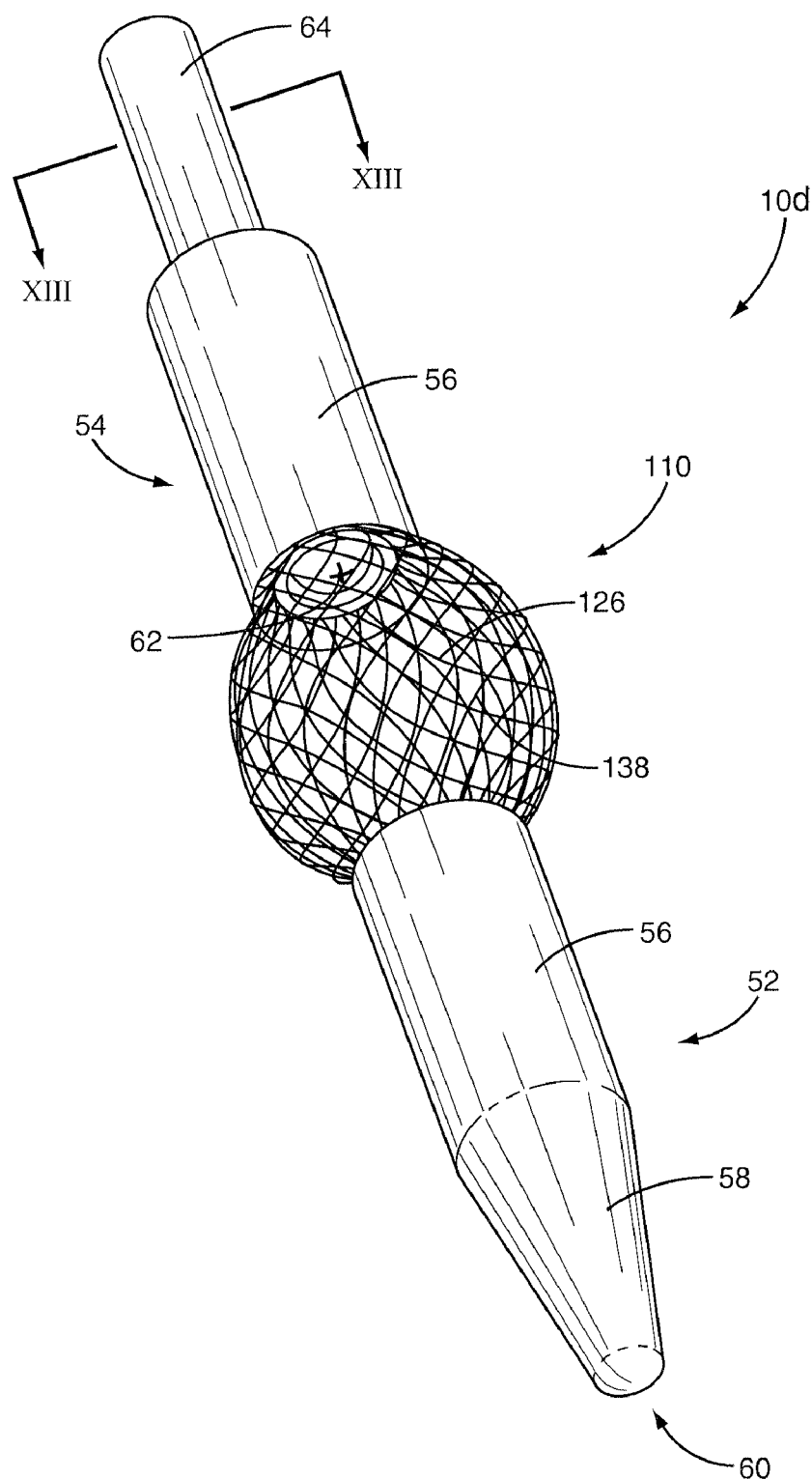
FIG. 12 is perspective view of a spinal rod according to one embodiment.
Figure 13:
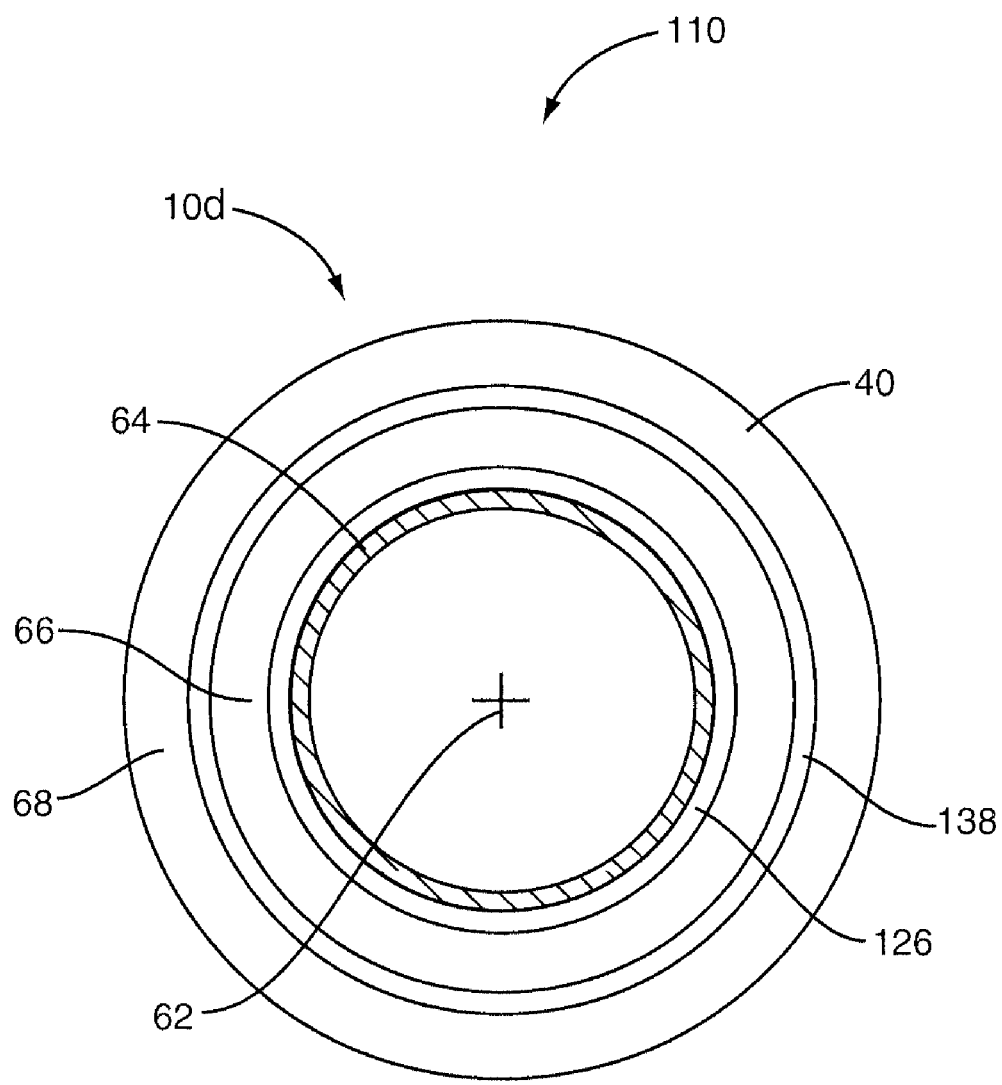
FIG. 13 is an end view of a spinal rod according to one embodiment.

In one embodiment, the rod holder 82 is cannulated to allow a surgeon to introduce an injectable substance through the rod holder 82 and into the rod 10c. A needle or other injection instrument is used to inject the injectable substance into the port J in the rod holder 82. Alternatively, a catheter may be inserted through the cannulated rod holder 82. Once the rod 10c is positioned as desired (possibly verified by fluoroscopy), the rod 10c may be inflated as described above. Alternatively, the rod 10c may be wholly or partially inflated with an injectable substance prior to insertion. In one embodiment, the injectable FIGS. 12 and 13 illustrate an alternative embodiment of an inflatable rod 10 comprising dissimilar end members 52, 54 on opposite sides of an inflatable portion 110. The first and second rod ends 52, 54 include a clamping portion 56. The clamping portions 56 may have similar widths and may further have a substantially similar cross section. Further, first rod end 52 includes a tapered portion 58 that decreases in width from the clamping portion 56 towards a distal end 60. The tapered portion 58 may improve the ease with which the rod 10d is inserted, such as when inserted longitudinally using the percutaneous techniques disclosed herein. The clamping portion 56 may be sized to fit within conventional rod securing devices such as the bone screws 14 shown in FIG. 1 and described above. For example, the clamping portion 56 may have a diameter within a range between about 4 and 7 mm. The rod ends 52, 54 may be constructed from a variety of surgical grade materials. These include metals such as stainless steels, cobalt-chrome, titanium, and shape memory alloys. Non-metallic rods, including polymer rods made from materials such as PEEK and UHMWPE, are also contemplated. The spinal rod 10 may have rigid or flexible rod ends 52, 54.

The inflatable portion 110 may have a structure similar to one or more of the embodiments disclosed above. That is, the inflatable portion 110 may have a substantially impermeable balloon structure 126 that can be collapsed diametrically for delivery and expanded in situ during implantation. The inflatable portion 110 may have one or more layers of reinforcing structure 138 that may be embodied as a braided, mesh, or woven structure as described above. Further, the exemplary inflatable portion 110 may comprise thin, reinforcing rails 32 running longitudinally along the inflatable portion 126, though none are specifically shown in FIG. 12.

FIG. 12 depicts an embodiment of the spinal rod 10d with the inflatable portion 110 in an inflated state. An injectable substance may be inserted into the inflatable portion 110 through a self-sealing valve 62 that is disposed within the visible, which suggests that the inflatable portion 110 may collapse to a size that is thinner than the overall width of the first and second end portions 52, 54. In the expanded state, the inflatable portion 110 extends wider than the first and second end portions 52, 54, which may provide some off-axis stability in compression. In one embodiment, the injectable substance contained within the inflatable portion 110 retains some flexibility after curing, which assists in a dampening effect of the rod 10d. With this configuration, the spinal rod 10d may replicate some of the stability that is provided by a facet joint in a healthy subject.

FIG. 13 shows an end view of the spinal rod 10d, looking into the proximal end of the second end member 54. In the illustrated embodiment, the expandable members 126, 138 of the inflatable portion 110 are disposed between concentric columns 64, 66, 68. Three columns 64, 66, 68 are shown, though more or fewer columns may be used. In the embodiment depicted, the balloon 126 is disposed between an inner column 64 and an intermediate column 66. The reinforcing structure 138 is disposed between the intermediate column 66 and an outer column 68. In other embodiments, the reinforcing structure 138 and the balloon 126 may be disposed between the same two column members 64, 66 or 66, 68. In one embodiment, the inflatable portion 110 does not include reinforcing structure 138. As suggested above, other embodiments may include a balloon 126 that has a reinforcing structure 138 embedded therein.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, embodiments disclosed herein have contemplated one balloon structure 26, 126, perhaps with one or more rails 32 or reinforcing structures 38, 138. In other embodiments, multiple concentric layers of balloons 26, 126 may be used. Also, the illustrated embodiment provided in FIGS. 12 and 13 include a single intermediate section between end portions 52, 54. In an alternative embodiment, the rod may comprise multiple intermediate sections disposed between additional clamping portions 56. The present embodiments are, therefore, to be considered in all respects as illustrative and not restrictive, and all changes coming within the meaning and equivalency range of the appended claims are intended to be embraced therein.

What is claimed is:

1. A spinal rod comprising:
    an inflatable member defining an interior cavity being constructed to contain a substance and having a length defined along a longitudinal axis between a first end and a second end, the inflatable member being constructed of a deformable material;
    a plurality of elongated rails positioned within the interior cavity and oriented along the longitudinal axis;
    a joining member positioned at an angle to the longitudinal axis and joining at least two of the plurality of elongated rails at a discrete point along each of the at least two elongated rails;
    the plurality of rails preventing the interior cavity from collapsing axially along the longitudinal axis during insertion of the spinal rod into a subject; and
    non-inflatable first and second end members connected to opposing sides of the inflatable member and being aligned with the longitudinal axis of the inflatable member;
    the first and second end members each include a width that is greater than the inflatable member in a non-inflated state and that is less than the inflatable member in an inflated state;
    the inflatable member extends through an interior of the second member away from the interior cavity.

2. The spinal rod of claim 1 wherein the plurality of rails are substantially parallel to a longitudinal axis of the inflatable member.

3. The spinal rod of claim 1 wherein the joining member is flexible to allow for radial movement of the plurality of rails during insertion into the subject.

4. The spinal rod of claim 1 wherein the joining member is rigid to maintain a spacing between the rails.

5. The spinal rod of claim 1 wherein the joining member is circumferentially positioned within the interior cavity.

6. The spinal rod of claim 1 wherein the joining member is obliquely disposed relative to the longitudinal axis.

7. The spinal rod of claim 1 wherein the first and second end members are constructed from a metal.

8. The spinal rod of claim 1 wherein the first and second end members are constructed from a non-metallic material.

9. The spinal rod of claim 1 wherein the first end member includes a tapered portion spaced away from the inflatable member that decreases in width towards a distal end.

10. A spinal rod comprising:
- an inflatable member defining an interior cavity being constructed to contain a substance and having a length defined along a longitudinal axis between a first end and a second end, the inflatable member being constructed of a deformable material;
- a plurality of elongated rails adjacent to the inflatable member and oriented along the longitudinal axis;
- a joining member positioned at an angle to the longitudinal axis and joining at least two of the plurality of elongated rails at a discrete point along each of the at least two elongated rails,
- the inflatable member expandable between a first orientation with the interior cavity having a first cross sectional size and a second orientation with the interior cavity having a larger second cross sectional size,
- the elongated rails being radially movable between the first and second orientations and having an axial stiffness to prevent the interior cavity from collapsing axially along the longitudinal axis during insertion of the spinal rod into a subject; and
- a first non-inflatable end member connected to a distal end of the inflatable member and aligned with the longitudinal axis of the inflatable member, the first non-inflatable end member including a cylindrical clamping portion adjacent to the inflatable member and a tapered portion that decreases in width away from the clamping portion, the first non-inflatable end member includes a greater width than the inflatable member in the first orientation;
- a second non-inflatable end member connected to a proximal end of the inflatable member and aligned with the longitudinal axis of the inflatable member, the second non-inflatable end member includes inner and outer concentric columns;
- a section of the inflatable member extending into an interior of the second non-inflatable end member and positioned between the inner and outer concentric columns of the second non-inflatable end member, the section in the interior of the second non-inflatable end member being constrained from expanding to the second orientation.

11. The spinal rod of claim 10 wherein the plurality of rails are substantially parallel to a longitudinal axis of the inflatable member.

12. The spinal rod of claim 10 wherein the joining member is flexible to allow for radial movement of the plurality of rails during insertion into the subject.

13. The spinal rod of claim 10 wherein the joining member is rigid to maintain a spacing between the rails.

14. The spinal rod of claim 10 wherein the joining member extends completely around the inflatable member.

15. The spinal rod of claim 10 wherein the joining member is obliquely disposed relative to the longitudinal axis.

16. The spinal rod of claim 10 wherein the plurality of rails are positioned interior to the inflatable member.

17. The spinal rod of claim 10 wherein the plurality of rails are positioned exterior to the inflatable member.

18. The spinal rod of claim 10 wherein the plurality of rails are adhered to the inflatable member.

19. A spinal rod comprising:
- a first end member comprising a first width;
- a second end member comprising a second width; and
- an intermediate section connected to the first and second end members; and
- a port operatively connected to the intermediate section;
- the intermediate section being diametrically expandable upon the introduction of a substance through the port, the intermediate section being expandable to a third width that is greater than the first and second widths, the intermediate section including an inner expandable member positioned within an outer expandable member;
- the first and second end members each being non-inflatable and wider than the intermediate section prior to the introduction of the substance;
- the inner and outer expandable members each extend into an interior of the second end member.

20. The spinal rod of claim 19 wherein the intermediate section initially includes a width prior to introduction of the substance that is less than the first and second widths.

21. The spinal rod of claim 19 wherein the first width and the second width are substantially the same.

22. The spinal rod of claim 19 wherein the first end member includes a tapered portion that decreases in width towards a distal end.

* * * * *